United States Patent
Karin et al.

(10) Patent No.: US 6,603,589 B2
(45) Date of Patent: Aug. 5, 2003

(54) CIRCULAR SCANNING PATTERNS

(75) Inventors: Jacob Karin, Ramat Gan (IL); Arie Shahar, Moshav Magshimim (IL); Gilad Golan, Rishon Le-Zion (IL)

(73) Assignee: Tokyo Seimitsu (Israel) Ltd., Hertzliya (IL)

( * ) Notice: Subject to any disclaimer, the term of this patent is extended or adjusted under 35 U.S.C. 154(b) by 0 days.

(21) Appl. No.: 10/159,042

(22) Filed: Jun. 3, 2002

(65) Prior Publication Data

US 2003/0099022 A1 May 29, 2003

Related U.S. Application Data

(60) Provisional application No. 60/331,552, filed on Nov. 19, 2001.

(51) Int. Cl.$^7$ .............................................. G02B 26/08
(52) U.S. Cl. ..................... 359/212; 359/201; 359/216; 359/900; 356/237.1
(58) Field of Search .................... 359/201–203, 359/212–219, 223, 226, 900; 356/237.1, 237.2–237.5, 239.7, 239.8, 388, 426, 428–431

(56) References Cited

U.S. PATENT DOCUMENTS 6,310,710 B1     10/2001    Shahar et al.
6,466,352 B1 * 10/2002    Shahar et al. ............... 359/212

* cited by examiner

Primary Examiner—James Phan
(74) Attorney, Agent, or Firm—Mark M. Friedman

(57) ABSTRACT

A method to compare similar physical areas of an inspection area using a scanning arrangement. The inspection area has a periodic pattern having a repeat vector. The scanning arrangement has a stage, a drive mechanism and at least one circular scanner. The circular scanner has a scanning head and an axis of rotation about which the scanning head performs a circular scanning motion. The drive mechanism is configured to provide relative movement between the stage and the axis of rotation. The method includes the steps of: scanning the inspection area by a combination of circular scanning of the scanning head and by generating relative movement between the stage and the axis of rotation such that pairs of curved scanning paths are related by an integer multiple of the repeat vector; and comparing at least one of said pairs of the curved scanning paths by a pixel to pixel comparison.

12 Claims, 15 Drawing Sheets

Prior Art

Prior Art

CIRCULAR SCANNING PATTERNS

This application claims the benefit of U.S. Provisional Application No. 60/331,552 filed Nov. 19$^{th}$, 2001.

FIELD AND BACKGROUND OF THE INVENTION

The present invention relates to a method of inspecting surfaces and, in particular, it concerns a method for inspecting surfaces having a periodic pattern such as dies and cells that are produced on the surface of silicon wafers used in the Integrated Circuits (IC) industry.

Many known inspection methods for defect detection are based on a comparison principal. According to this principal the gray levels of each pixel in the digital image acquired from the inspection region are subtracted from the gray levels of their corresponding pixels in a digital reference-image related to the inspection region. A defect is indicated if the subtraction results for any pixel of the digital image are greater than a predetermined threshold value.

When the acquired image of the inspection region contains a large amount of pixels due to one or a combination of the size of the inspection region or high resolution of the image, the reference-image has to be stored in a large volume memory which is very expensive.

For some applications such as high-resolution inspection of silicon wafers, the cost of large volume memory makes the use of the above methods impractical. An alternative inspection method is also based on a comparison technique and is useful for surfaces having a periodic pattern. In this method, the scan is performed along stripes or bands known as swaths. The swaths are aligned with the periodic structure of the periodic pattern. Since the pattern contains many periodic fragments, such as cells or dies and the swaths are relatively narrow, the information in the swath relating to each periodic fragment is dramatically reduced. As the inspection area has a periodic pattern, the surface can be inspected by making a comparison between swaths that are in related fragments of the periodic pattern. Accordingly, this comparison method requires a relatively small memory-volume and it also eliminates the need for a reference-image.

A difference detected by a comparison between two fragments indicates that one of the fragments is defective, but the defective fragment is not identifiable. Three-fragment comparison is needed to identify the fragment and the defect location within the identified fragment and not just to detect the existence of a defect without the ability to indicate the exact location of the defect. Three-fragment comparison is performed by comparing the fragment under inspection with two adjacent fragments. Statistically, it is assumed that there is a very low probability that a defect will repeat itself at the same position in two other fragments. Therefore, a defect is defined as a deviation that appears twice in the two comparisons and the fragment that contains the defect is the one that differs from the other two fragments. The three-fragment comparison method is also known as Cell-to-Cell or Die-to-Die comparison. The three-fragment comparison method is only effective when the scan direction of the swaths is aligned with a periodic structure that typically has Cartesian symmetry.

In the IC industry there is continuing demand for miniaturization of the wafer patterns. This is leading to a reduction in the dimensions of electrical components produced on silicon wafers. Therefore, there is a need for improving the detection capability of the inspection machines by improving resolution, signal to noise ratio and contrast. Moreover, the quantity of inspection data is increasing with the increase in resolution and therefore there is a need for inspection machines with a higher throughput.

Recently a novel scanning system was described in a U.S. Pat. No. 6,310,710 to Shahar et al., entitled "High-Resolution Reading and Writing Using Rotating Beams and Lenses Rotating at Equal or Double Speed". The aforementioned system provides better resolution and higher throughput as compared to other scanning systems. Accordingly, the aforementioned system is very attractive to the IC industry for fulfilling the current and future demands in the field of silicon wafers inspection. The scanning system described in the aforementioned system is a circular scanner including at least one scanning beam that is operated with or without confocal mode. The circular scanner produces a scan along a circular path and therefore does not have the symmetry of a Cartesian coordinate system. Therefore, performing the Cell-to-Cell or Die-to-Die comparison method with the rotating microscope leads to a mismatch between the circular paths of the scanner and the orthogonal symmetry of the silicon wafers. Therefore, large quantities of inspection data need to be stored relating to the area of several dies. Therefore a very large memory-volume is required, which makes the use of the circular scanner impractical, in spite of all its advantages.

Reference is now made to FIG. 1 and FIG. 2. FIG. 1 is a side view of a scanning arrangement 5 configured to perform circular scanning paths that is constructed and operable in accordance with the prior art. FIG. 2 is a plan view of scanning arrangement 5. Scanning arrangement 5 includes a circular scanner 6, a stage 19 and a drive mechanism 21 (not shown). Circular scanner 6 includes a spindle 8, a polygon 10, a disk 12 and at least one scanning head 14. Circular scanner 6 has an axis of rotation 15 about which the rotating elements of circular scanner 6 rotate. Spindle 8 rotates polygon 10 at a rate W about axis of rotation 15. Spindle 8 rotates disk 12 at a rate 2 W about axis of rotation 15. Disk 12 carries scanning head 14. Therefore, scanning head 14 performs a circular scanning motion about axis of rotation 15 due to the rotation of disk 12 over an inspection area 18 of a sample. The sample containing inspection area 18 is mounted on stage 19. Drive mechanism 21 is configured to provide relative linear movement between stage 19 and axis of rotation 15 in a direction perpendicular to axis of rotation 15 in order to enable circular scanner 6 perform an area scan. Circular scanner 6 also includes a light source 20, an optical apparatus 24, an auto focus system 26 and a light detector 30. The optical path of a light beam 16 originates from light source 20. Light beam 16 is transmitted from light source 20 through optical apparatus 24 and optional auto focus system 26 to polygon 10. Light beam 16 is reflected by the surfaces of polygon 10 along a path 32 to scanning head 14 (FIG. 2). It is shown in the prior art that path 32 is equivalent to a path 34 and therefore circular scanner 6 preserves the length of the optical path of light beam 16 at all times (FIG. 2). Light beam 16 is projected to a point 28 which is on inspection area 18 by scanning head 14. Light beam 16 is reflected from inspection area 18 via scanning head 14, polygon 10, auto focus system 26 and optical apparatus 24 to light detector 30. Light beam 16 is a single beam or a collection of multiple beams. The scanning path produced by light beam 16 is referred to as a scanning swath. If light beam 16 includes a collection of multiple beams, then the scanning path produced by each multiple beam is referred to as a curved scanning path. Therefore, if light beam 16 includes a collection of multiple beams, there will be a plurality of curved scanning paths per scanning swath.

Reference is now made to FIG. 3, which is a schematic plan view of a scanning pattern 35 produced by scanning arrangement 5 in accordance with the prior art. This particular example describes a system having four scanning beams included within light beam 16. Circular scanner 6 scans inspection area 18 by moving a light spot 38, a light spot 40, a light spot 42 and a light spot 44 along a curved scanning path 46, a curved scanning path 48, a curved scanning path 50 and a curved scanning path 52 respectively. Inspection area 18 has Cartesian symmetry is composed of a periodic pattern which is schematically shown as a plurality of blocks 54.

Reference is now made to FIG. 4, which is a schematic plan view of an area scanning pattern 56 produced by scanning arrangement 5 in accordance with the prior art. In order to produce area-scanning pattern 56, relative linear motion between the axis of rotation 15 (FIG. 1) and stage 19 (FIG. 1) is introduced between each scanning swath performed by circular scanner 6. This particular example also describes a system having four scanning beams included within light beam 16. Area scanning pattern 56 includes a plurality of successive scanning swaths 58, 60, 62, 64 and 66 produced by rotating disk 12. Relative movement is generated between axis of rotation 15 and stage 19 between the production of each of scanning swaths 58, 60, 62, 64 and 66. It is seen that a comparison between successive scanning swaths 58, 60, 62, 64 and 66 is not useful since they do not scan similar physical areas on inspection area 18. The only way to perform a comparison is by storing large amounts of information and to detect the matching physical areas stored in the information.

There is therefore a need for a method to inspect surfaces having a periodic pattern with a first type of symmetry, such as an IC wafer having the symmetry of a Cartesian coordinate system, using a scanner having a second type of symmetry, such as circular scanner, while keeping the memory requirements and processing power at a reasonable level.

SUMMARY OF THE INVENTION

The present invention is a method for inspecting surfaces having a periodic pattern.

According to the teachings of the present invention there is provided, a method to compare similar physical areas of an inspection area of a sample using a scanning arrangement, the inspection area having a periodic pattern having a repeat vector, the scanning arrangement having a stage configured for mounting the sample thereon, the scanning arrangement having a drive mechanism and at least one circular scanner, the circular scanner having at least one scanning head and an axis of rotation, the scanning head performing a circular scanning motion about the axis of rotation, the drive mechanism configured to provide relative movement between the stage and the axis of rotation, the method comprising the steps of: (a) scanning the inspection area by a combination of circular scanning of the scanning head and by generating relative movement between the stage and the axis of rotation so as to generate a scanning pattern which includes a plurality of curved scanning paths wherein pairs of the curved scanning paths are related by an integer multiple of the repeat vector; and (b) comparing at least one of the pairs of the curved scanning paths by a pixel to pixel comparison.

According to a further feature of the present invention: (a) the at least one circular scanner is implemented as at least two circular scanners; and (b) the axes of rotation of the at least two circular scanners are separated by a multiple of the repeat vector.

According to a further feature of the present invention: (a) the axes of rotation of the at least two circular scanners are connected by a line which is parallel to the repeat vector; and (b) the relative movement between the stage and the axes of rotation is generated in a direction which is parallel to the repeat vector.

According to a further feature of the present invention: (a) the axes of rotation of each of the at least two circular scanners are connected by a line which is parallel to the repeat vector; and (b) the relative movement between the stage and the axis of rotation is generated in a direction which is perpendicular to the repeat vector.

According to a further feature of the present invention the axes of rotation of the at least two circular scanners are separated by a distance substantially equal to a diameter of each of the curved scanning paths.

According to a further feature of the present invention the axes of rotation of the at least two circular scanners are separated by a distance less than a diameter of each of the curved scanning paths.

According to a further feature of the present invention: (a) the inspection area includes a plurality samples which are substantially identical, each of the samples having a key point, the repeat vector being the separation between key points of the samples; and (b) the method further includes the step of mounting the samples on the stage such that the key points of the samples are directed in the same direction.

According to a further feature of the present invention the step of scanning the inspection area is performed by scanning the inspection area by generating relative linear movement between the stage and the axis of rotation while at the same time performing circular scanning of the scanning head so as to generate a scanning pattern which includes a plurality of curved scanning paths wherein pairs of the curved scanning paths are related by an integer multiple of the repeat vector.

According to a further feature of the present invention the relative linear movement is at constant velocity.

According to a further feature of the present invention a first integer multiplied by a time taken to generate one of the curved scanning paths is substantially equal to a second integer multiplied by a time taken to advance the stage relative to the axis of rotation by a distance equal to the length of the repeat vector.

According to a further feature of the present invention the second integer is equal to one.

According to the teachings of the present invention there is also provided, a method to compare similar physical areas of an inspection area using a circular scanner, the inspection area including a plurality of samples, the samples being substantially identical, the circular scanner having a stage apparatus, a drive mechanism, at least one scanning head and an axis of rotation, the at least one scanning head performing a circular scanning motion about the axis of rotation, the stage apparatus having at least two stage portions, the drive mechanism configured to provide relative movement between each of the stage portions and the axis of rotation, the method comprising the steps of: (a) mounting the samples on the stage apparatus such that there is one of the samples per one of the stage portions such that the samples are disposed symmetrically around the axis of rotation; (b) scanning at least part of the samples by employing the scanning head to perform a substantially circular scanning path; (c) comparing at least two best matched curved scan paths on the substantially circular scanning path by a pixel to pixel comparison; and (d) moving the samples

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method for inspecting surfaces having a periodic pattern.

The principles and operation of the method for inspecting surfaces having a periodic pattern according to the present invention may be better understood with reference to the drawings and the accompanying description.

The principle of the methods of the present invention is to provide scanning patterns having similar physical areas of the inspection area under test in sequential curved scanning paths or swaths. Therefore, comparison of the inspection is performed between sequential swaths and the need to store large amounts of data is eliminated. It should be noted that although storage needs are minimized when adjacent or neighboring curved scanning lines and swaths are compared, the scope of this invention also relates to comparing swaths that are not adjacent to each other but relate to similar physical areas of the inspection area.

Figure 1:
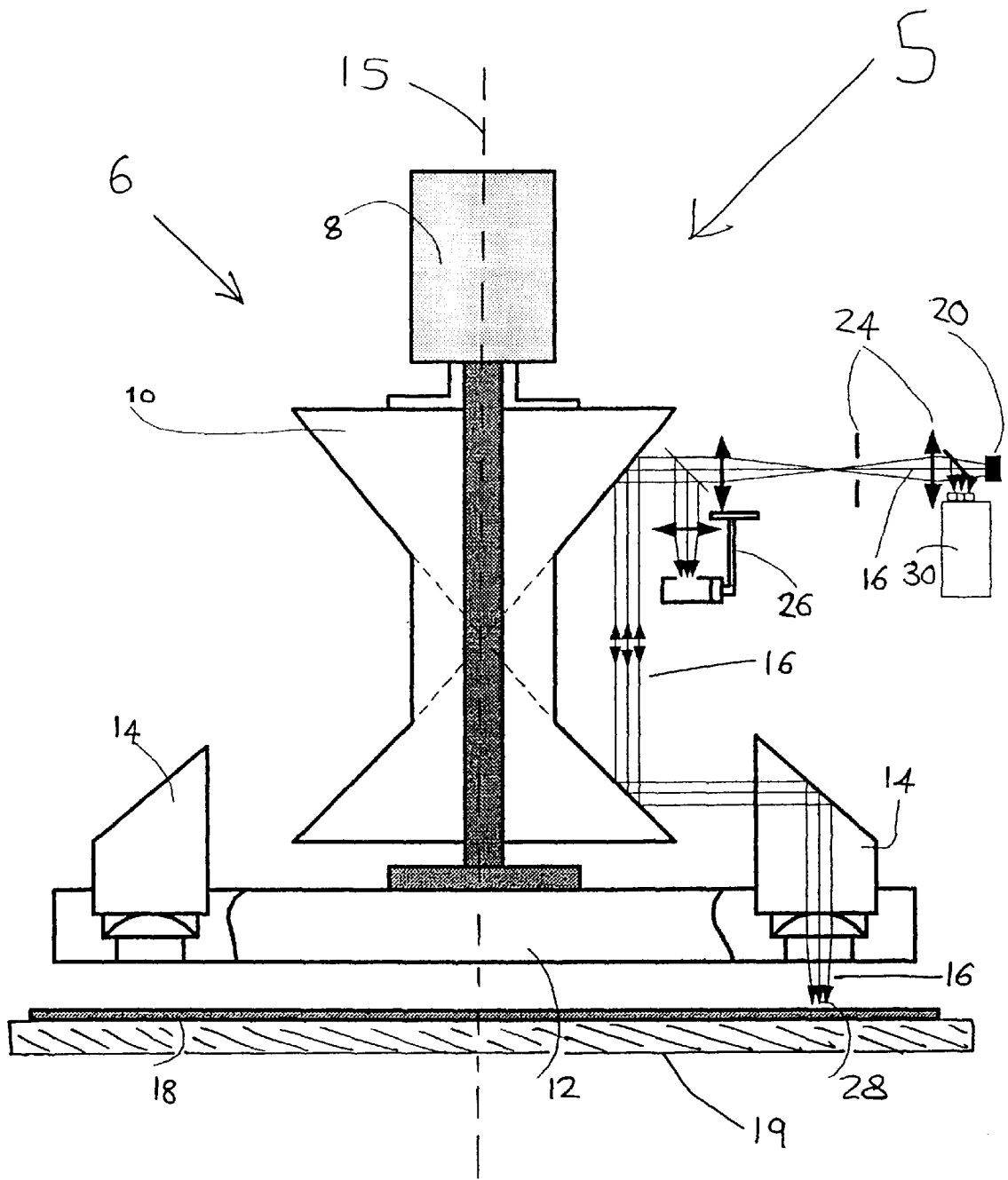
FIG. 1 is a side view of a scanning arrangement configured to perform circular scanning paths that is constructed and operable in accordance with the prior art.
Figure 2:
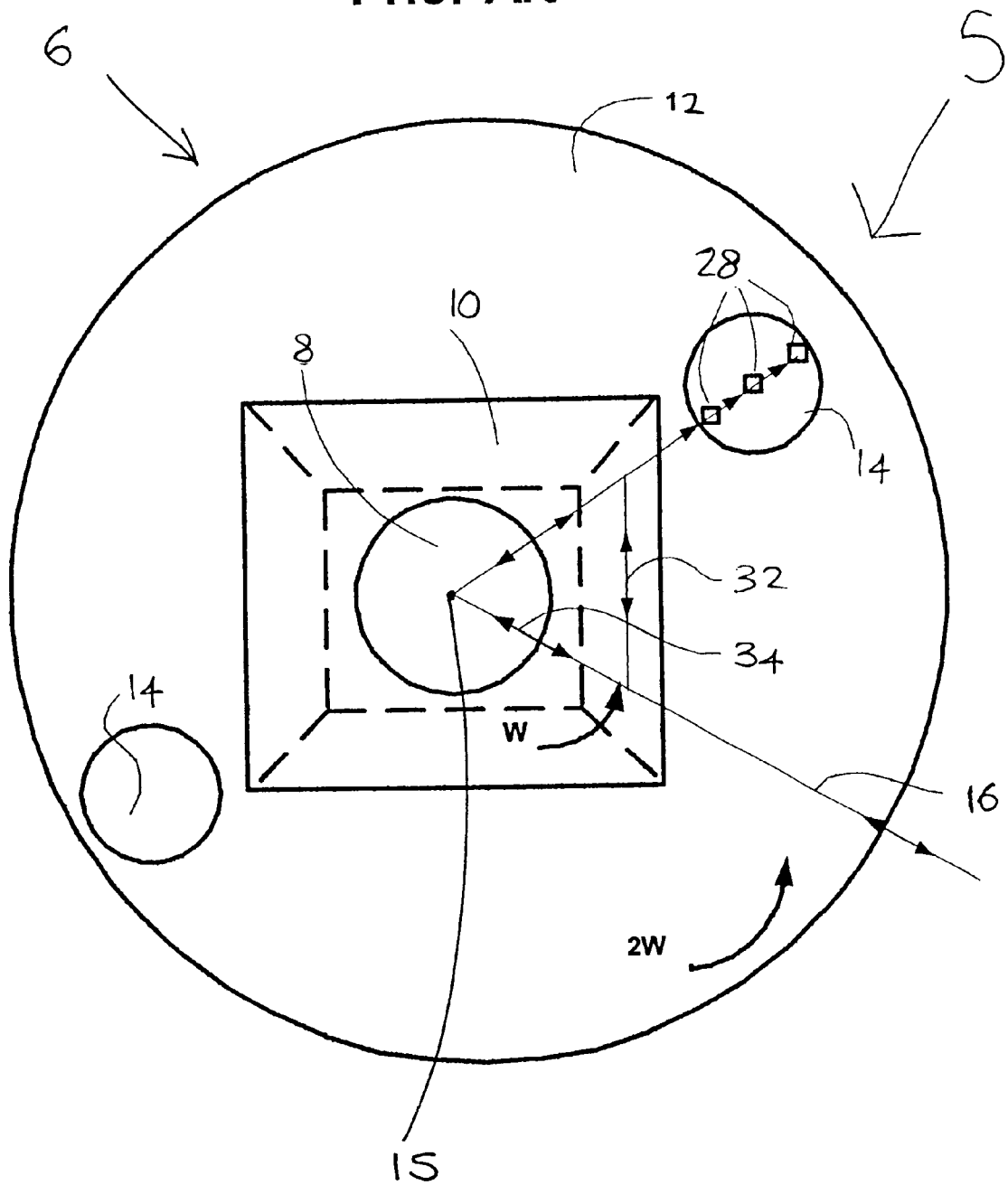
FIG. 2 is a plan view of the scanning arrangement of FIG. 1.
Figure 3:
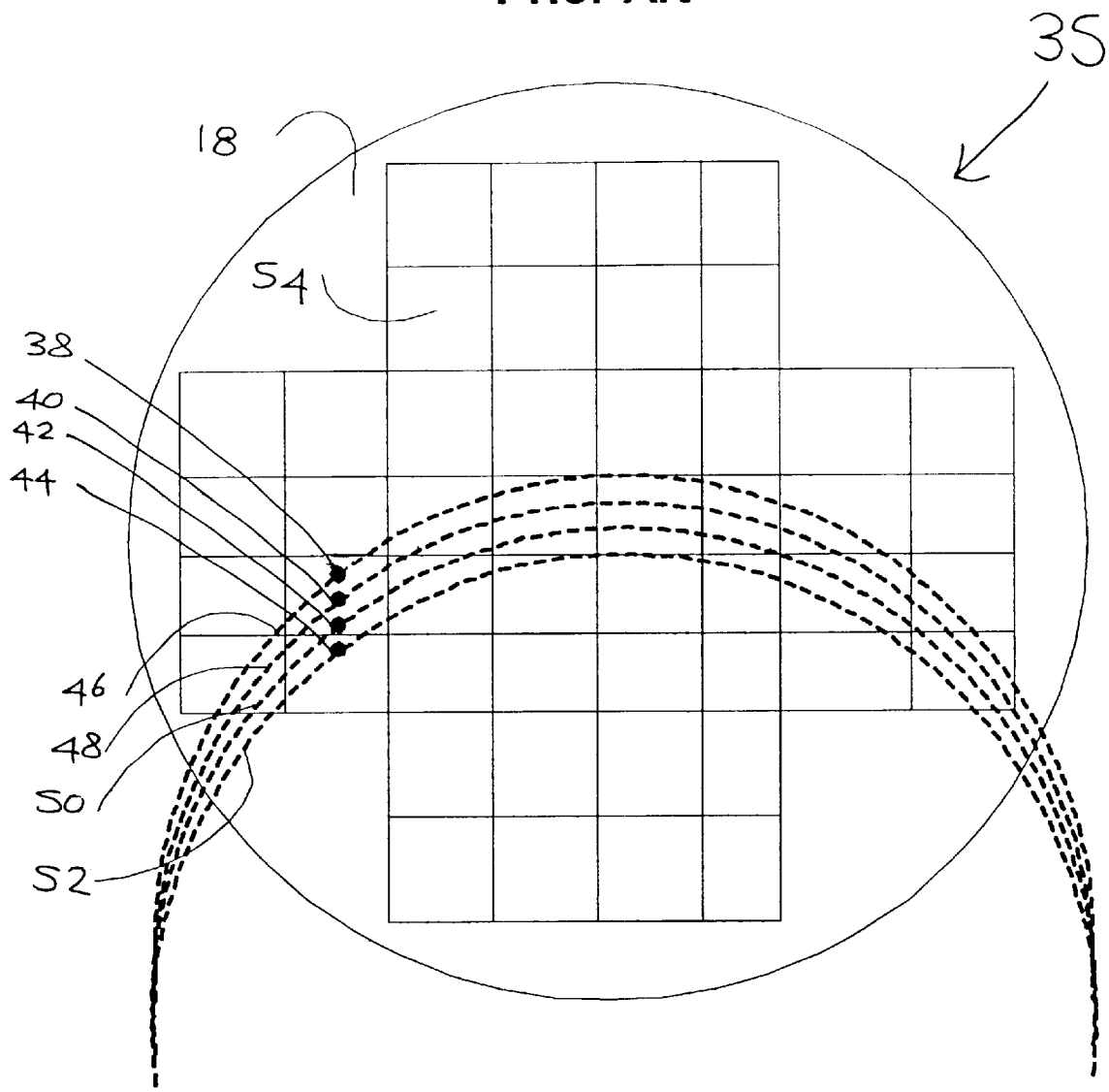
FIG. 3 is a schematic plan view of a scanning pattern produced by the scanning arrangement of FIG. 1.
Figure 4:
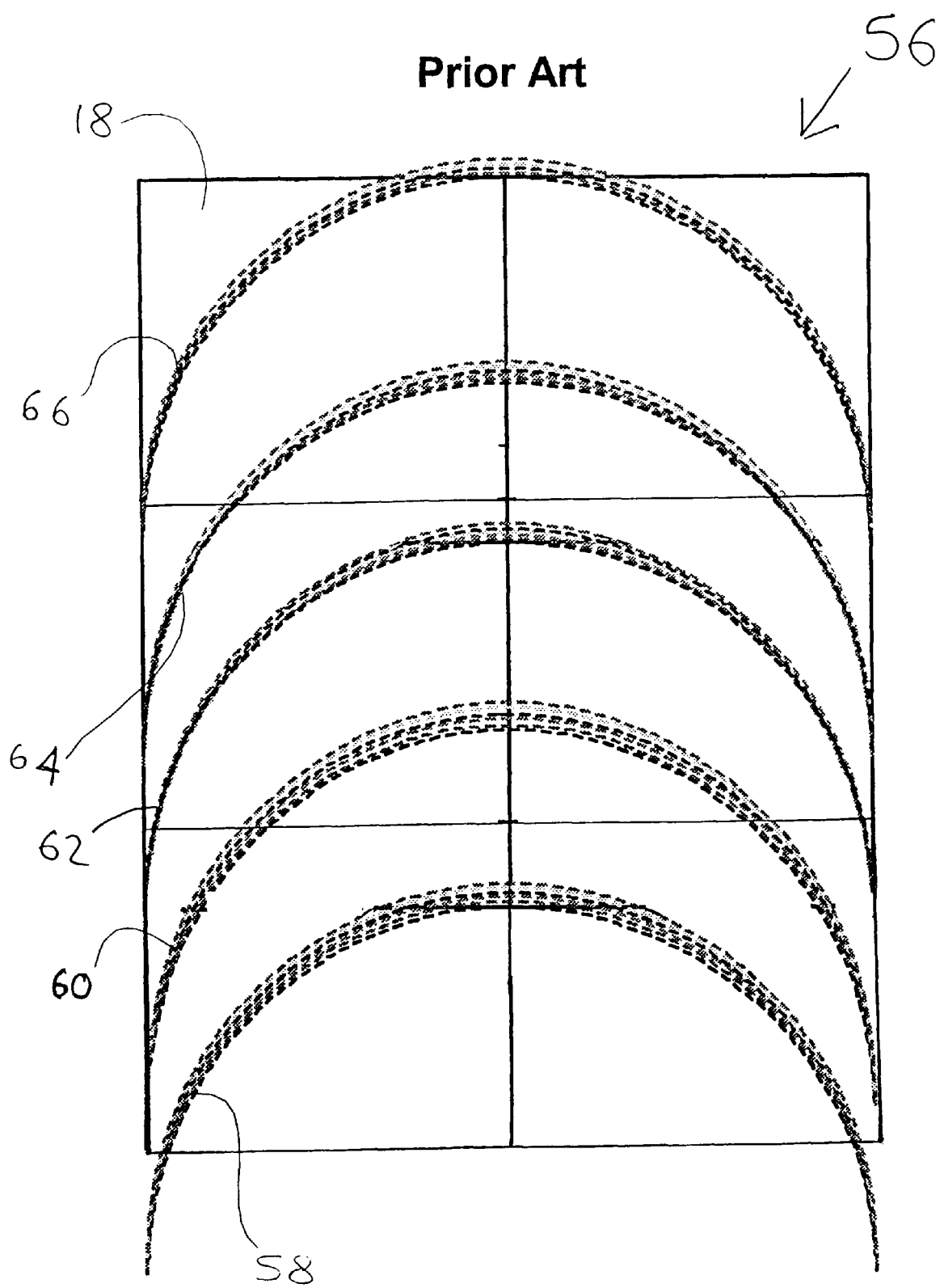
FIG. 4 is a schematic plan view of an area scanning pattern produced by the scanning arrangement of FIG. 1.

It should also be noted that with regard to prior art scanning arrangement 5, described with reference to FIG. 3, the alignment of light spots 38, 40, 42 and 44 is preserved throughout the scanning period. In other words, the line connecting the light spots 38, 40, 42 and 44 points in the same direction throughout the scanning period. However, the methods of the present invention are not limited to scanning arrangement 5 or similar circular scanners. Moreover, the principles of the present invention are applicable to inspect surfaces having a periodic pattern with a first type of symmetry using a scanner having a second type of symmetry. In other words, the principles of the present invention are not limited to a circular scanner or an inspection area having Cartesian symmetry.

Figure 5:
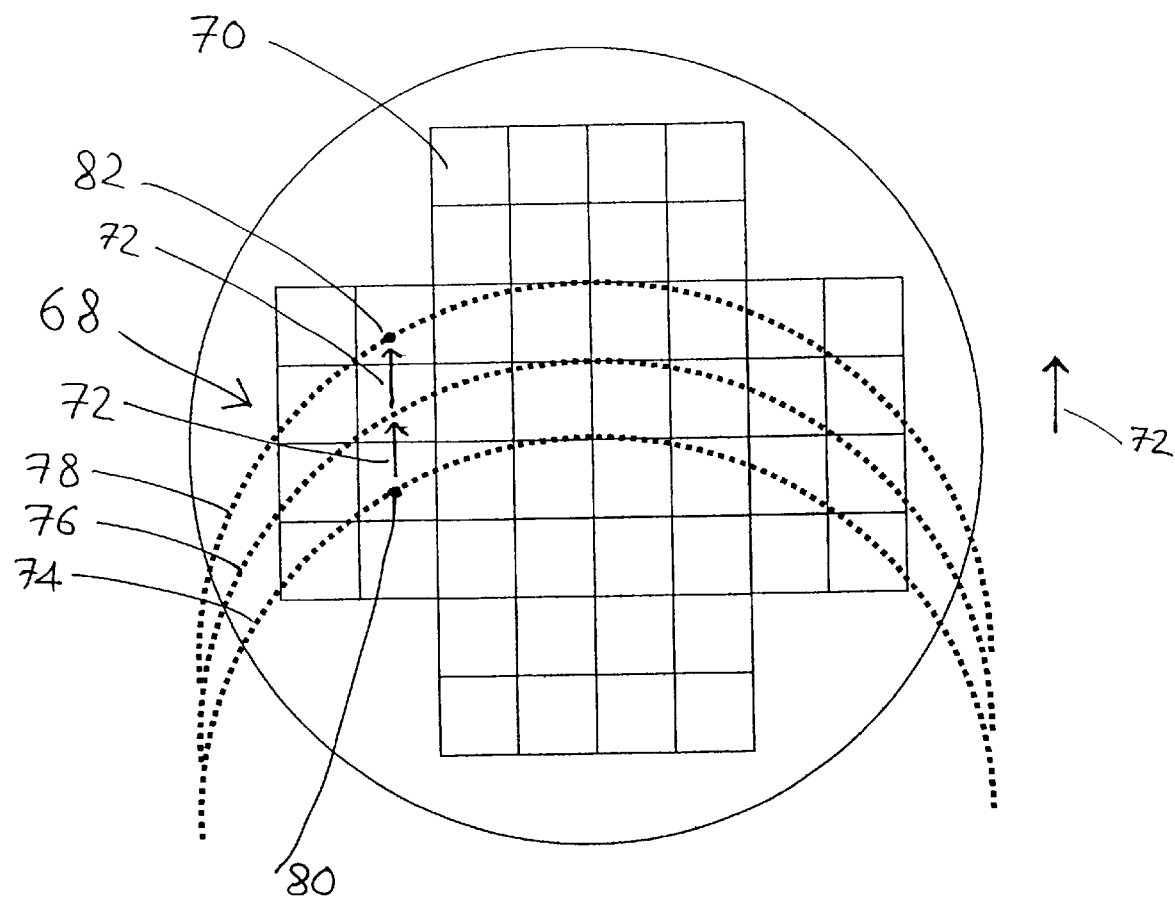
FIG. 5 is a schematic plan view of a scanning pattern produced by a circular scanner operating in a "step mode" in accordance with a preferred embodiment of the invention.

Reference is now made to FIG. 5, which is a schematic plan view of a scanning pattern 68 of an inspection area 70 produced by scanning arrangement 5 operating in a "step mode" in accordance with a preferred embodiment of the invention. Inspection area 70 has a periodic pattern. The periodic pattern of inspection area 70 has a repeat vector 72. Repeat vector 72 represents the direction and distance of repetition of similar physical areas of inspection area 70. The example presented here with reference to FIG. 5 describes comparing similar physical areas within a single sample. However, it is possible to compare similar physical areas over a plurality of samples. It should also be noted that the repetitive physical areas of inspection area 70 are described as "similar physical areas" due to the fact that they are only identical to the extent that there are no defects on inspection area 70. The method to compare similar physical areas of inspection area 70 using scanning arrangement 5 includes scanning inspection area 70 by a combination of circular scanning of scanning head 14 and by generating relative movement between stage 19 and the axis of rotation 15 so as to generate scanning pattern 68. Scanning pattern 68 includes a plurality of curved scanning paths, which include a curved scanning path 74, a curved scanning path 76 and a curved scanning path 78. Pairs of the curved scanning paths, for example a pair including curved scanning path 74 and curved scanning path 76, a pair including curved scanning path 76 and curved scanning path 78, and a pair including curved scanning path 74 and curved scanning path 78 are all related by a first integer multiple of repeat vector 72. The method further includes comparing at least one of the pairs of the curved scanning paths by a pixel to pixel comparison. For example, a pixel 80 located on curved scanning path 74 is compared with a pixel 82 located on curved scanning path 78. Pixel 80 and pixel 82 are separated by a distance of repeat vector 72 multiplied by two in the direction of repeat vector 72. It is also seen that pixel 80 and pixel 82 represent the same relative location within their own respective physical areas of inspection area 70. Scanning pattern 68 is produced by advancing the stage 19 relative to axis of rotation 15 in a distance equal to repeat vector 72 in a direction parallel to repeat vector 72. The resulting curved scanning paths 74, 76 and 78 relate to similar physical areas of inspection area 70 and therefore curved scanning paths 74, 76 and 78 are useful for direct comparison without the need to store large amounts of information. It should be noted that the method referred to with reference to FIG. 5 is also applicable to a scanner having more than one scanning head and/or each scanning swath including more than one curved scanning path.

Figure 6:
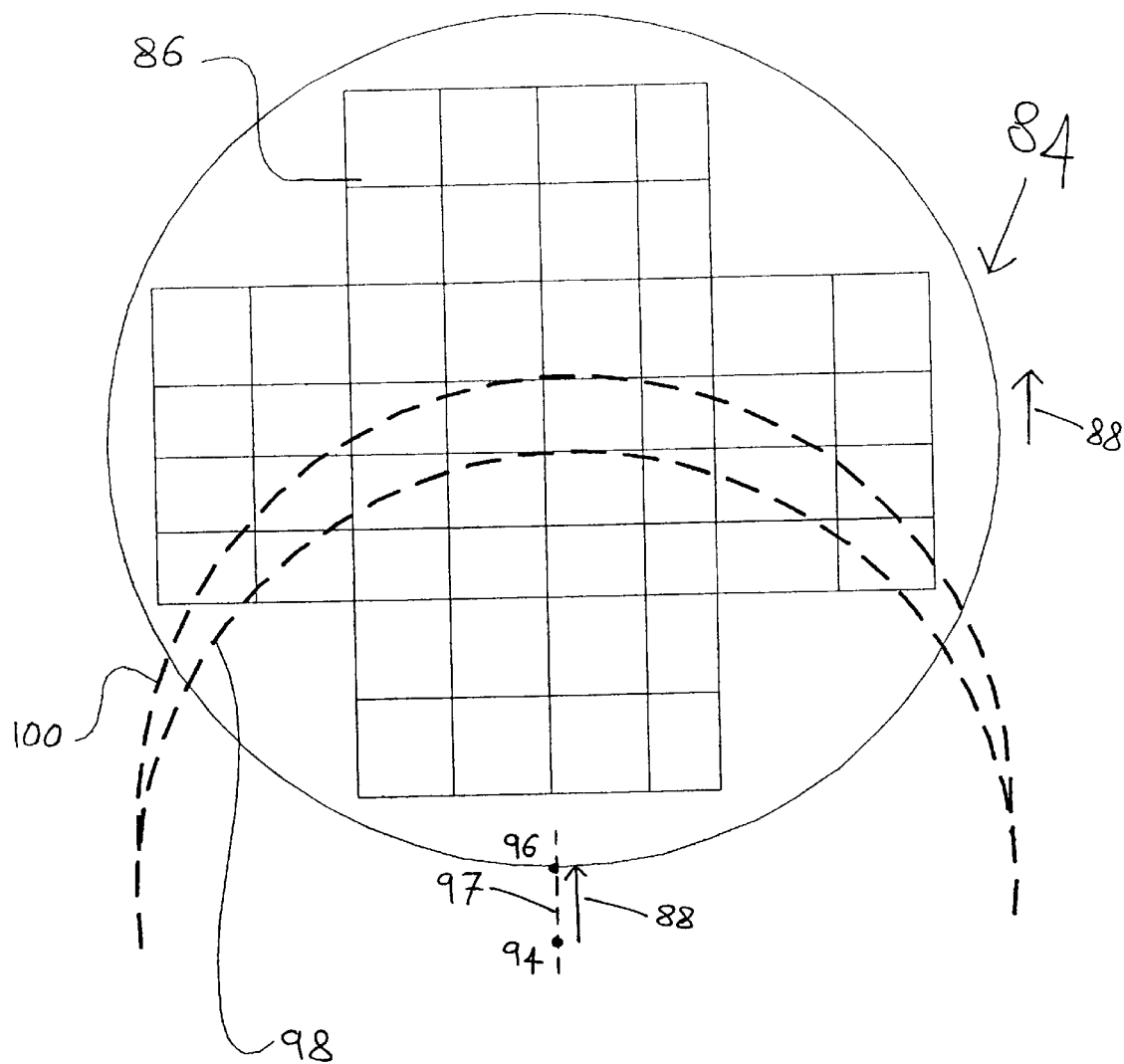
FIG. 6 is a schematic plan view of a scanning pattern produced by the operation of two circular scanners in a scan direction parallel to a repeat vector of an inspection area in accordance with a preferred embodiment of the invention.

Reference is now made to FIG. 6, which is a schematic plan view of a scanning pattern 84 of an inspection area 86 produced by scanning arrangement 5 in accordance with a preferred embodiment of the invention. Circular scanner 6 is replaced by two circular scanners, each being similar to circular scanner 6. Each of the two circular scanners has a scanning head, one of the circular scanners having a scanning head 90 (not shown) and an axis of rotation 94 and another of the circular scanners having a scanning head 92 (not shown) and an axis of rotation 96. Inspection area 86 has a periodic pattern. The periodic pattern of inspection area 86 has a repeat vector 88. Repeat vector 88 represents the direction and distance of repetition of similar physical areas of inspection area 86. Axis of rotation 94 and axis of rotation 96 are separated by a second integer multiple of repeat vector 88. In the example of FIG. 6 the second integer multiple is equal to one. Axis of rotation 94 and axis of rotation 96 are connected by a line 97, which is parallel to repeat vector 88. Circular scanning of scanning head 90 produces a curved scanning path 98. Circular scanning of scanning head 92 produces a curved scanning path 100. Typically curved scanning path 98 and curved scanning path 100 are produced simultaneously. Relative movement between stage 19 and axes of rotation 94, 96 is then generated in a direction which is parallel to repeat vector 88 and then another pair of curved scanning paths is produced. Therefore scanning pattern 84 is produced by simultaneous "double scan", where in each revolution of scanning heads 90, 92, two scanning swaths are produced that are separated from each other by repeat vector 88. The resulting curved scanning paths, for example curved scanning path 98 and curved scanning path 100, relate to similar physical areas of inspection area 86 and therefore curved scanning paths 98 and 100 are useful for direct comparison without the need to store large amounts of information. It should be noted that the method referred to with reference to FIG. 6 is also applicable to a scanning arrangement having more than two circular scanners and/or each circular scanner having more than one scanning head and/or each scanning swath including more than one curved scanning path.

Figure 7:
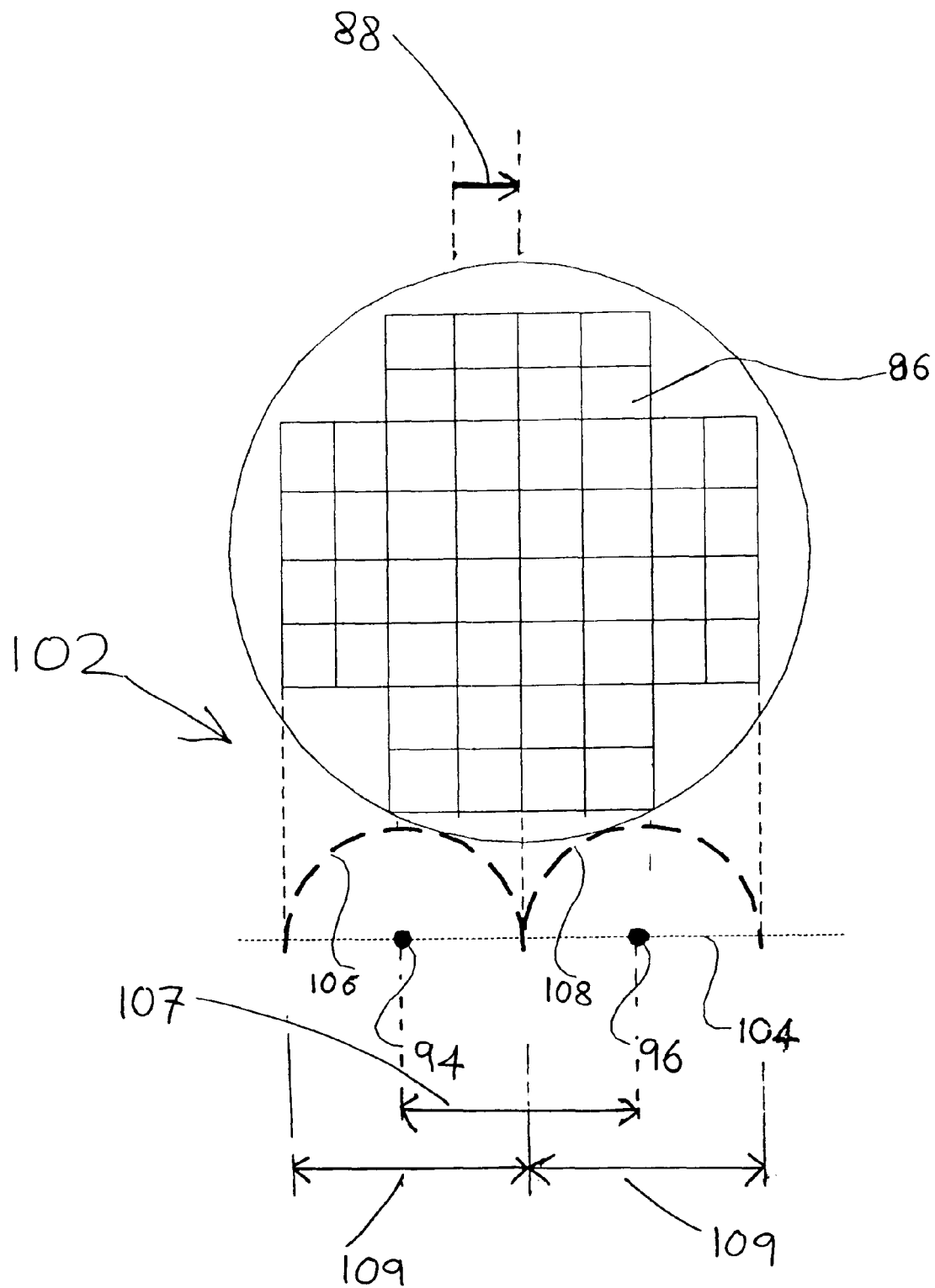
FIG. 7 is a schematic plan view of a scanning pattern produced by the operation of two circular scanners in a scan direction perpendicular to a repeat vector of an inspection area in accordance with a preferred embodiment of the invention.

Reference is now made to FIG. 7, which is a schematic plan view of a scanning pattern 102 of inspection area 86 produced by scanning arrangement 5. Scanning arrangement 5 has two scanners, one of the two scanners including scanning head 90 and another of the two scanners including scanning head 92. Axis of rotation 94 and axis of rotation 96 are separated by a third integer multiple of repeat vector 88. In the example of FIG. 7 the third integer multiple is equal to four. Axis of rotation 94 and axis of rotation 96 are connected by a line 104, which is parallel to repeat vector 88. Circular scanning of scanning head 90 produces a curved scanning path 106. Circular scanning of scanning head 92 produces a curved scanning path 108. Typically curved scanning path 106 and curved scanning path 108 are produced simultaneously. Relative movement between stage 19 and axes of rotation 94, 96 is then generated in a direction which is perpendicular to repeat vector 88 and then another pair of curved scanning paths is produced. Therefore scanning pattern 84 is produced by simultaneous "double scan", where in each revolution of scanning heads 90, 92, two scanning swaths are produced that are separated from each other by an integer multiple of repeat vector 88. The resulting curved scanning paths, for example curved scanning path 106 and curved scanning path 108, relate to similar physical areas of inspection area 86 and therefore curved scanning paths 106 and 108 are useful for direct comparison without the need to store large amounts of information. To prevent overlap of curved scanning path 106 and curved scanning path 108, axis of rotation 94 and axis of rotation 96 are separated by a distance 107 which is substantially equal to a diameter 109 of curved scanning path 106 and curved scanning path 108. It is preferably for scanning head 90 and scanning head 92 to rotate simultaneously in the same direction, thereby covering similar physical areas of inspection area 86. It should be noted that the method referred to with reference to FIG. 7 is also applicable to a scanning arrangement having more than two circular scanners and/or each circular scanner having more than one scanning head and/or each scanning swath including more than one curved scanning path.

Figure 8:
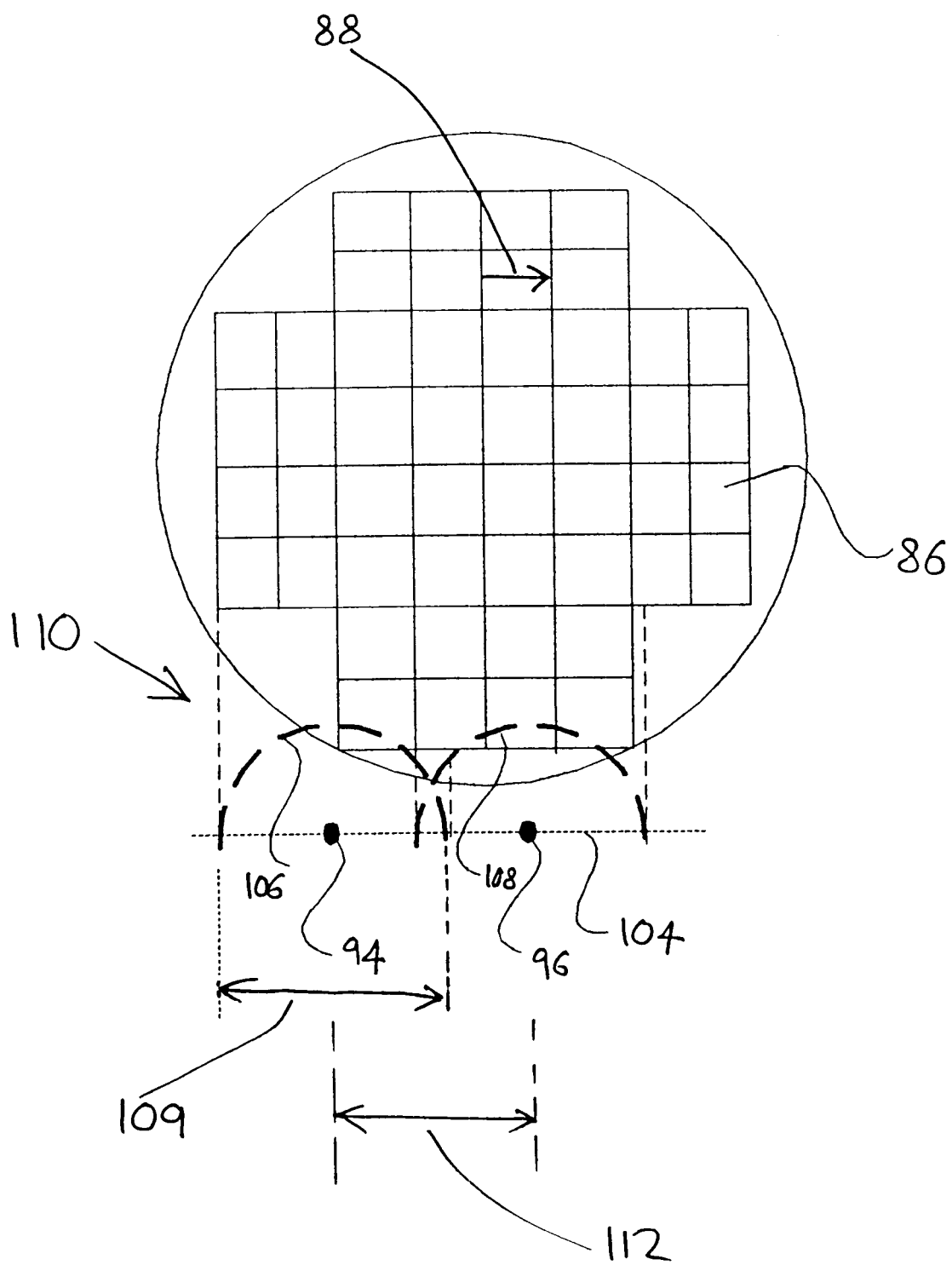
FIG. 8 is a schematic plan view of an overlapping scanning pattern produced by the operation of two circular scanners in a scan direction perpendicular to a repeat vector of an inspection area in accordance with a preferred embodiment of the invention.

Reference is now made to FIG. 8, which is a schematic plan view of an overlapping scanning pattern 110 of inspection area 86 produced by scanning arrangement 5. Scanning arrangement 5 has two scanners, one of the two scanners including scanning head 90 and another of the two scanners including scanning head 92. The method to produce overlapping scanning pattern 110 is the same as the method described with reference to FIG. 7 except that axis of rotation 94 and axis of rotation 96 are separated by a distance 112. Distance 112 is an integer multiple of repeat vector 88 and is less than diameter 109 of curved scanning path 106 and curved scanning path 108.

Figure 9:
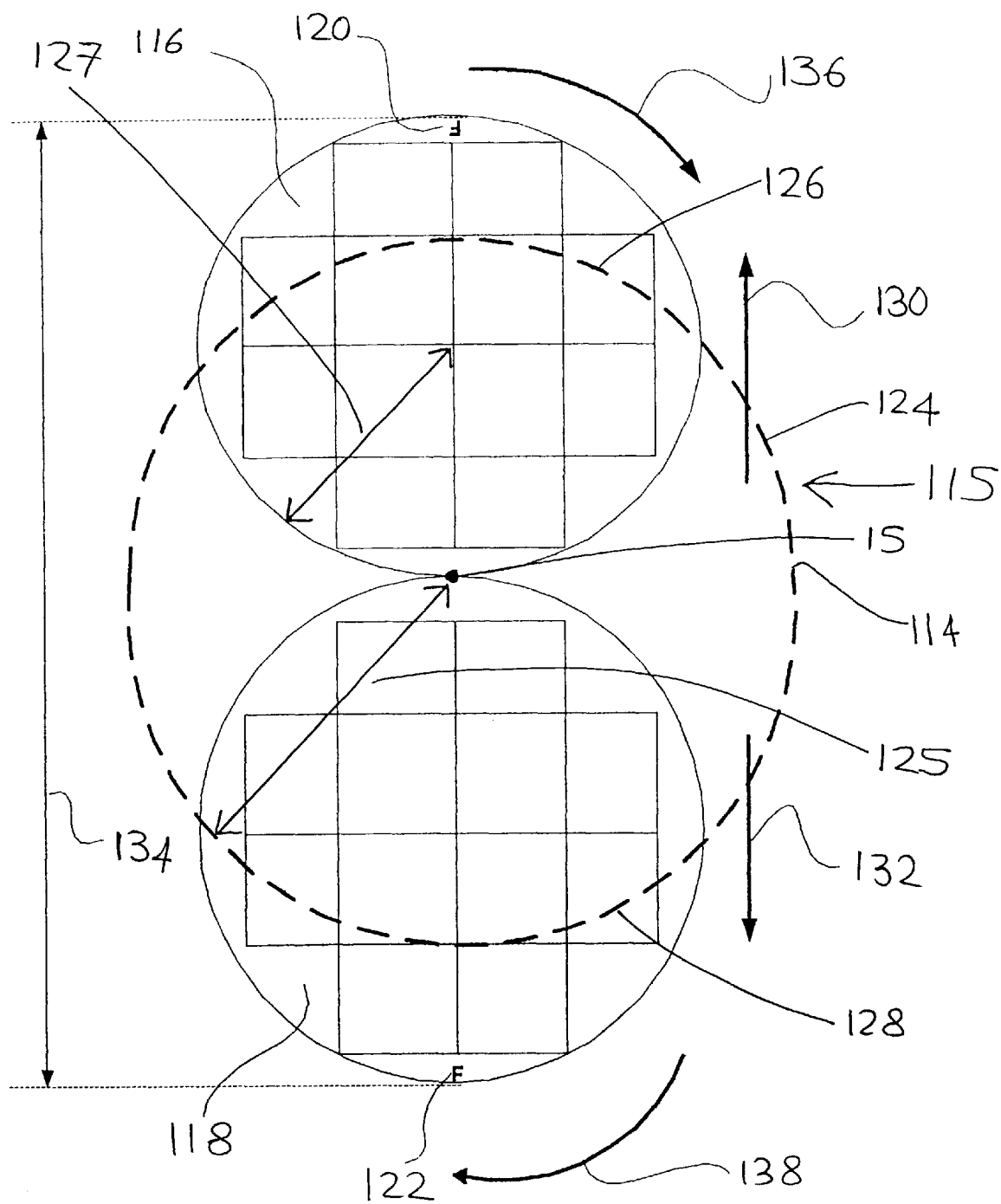
FIG. 9 is a schematic plan view of a circular scanning pattern produced by a circular scanner scanning two samples simultaneously in accordance with a preferred embodiment of the invention.

Reference is now made to FIG. 9, which is a schematic plan view of a circular scanning pattern 114 of an inspection area 115 produced by circular scanner 6 in accordance with a preferred embodiment of the invention. Inspection area 115 includes a plurality of samples 116, 118. Samples 116, 118 are substantially identical to the extent that there are no defects on samples 116, 118. Samples 116, 118 have a substantially identical pattern. Sample 116 has a key point 120. Sample 118 has a key point 122. Key point 120 and key point 122 represent the same relative point on sample 116 and sample 118 respectively. In other words, key point 120 and key point 122 represent points of common symmetry of samples 116, 118. Stage 19 is implemented as a stage apparatus (not shown). The stage apparatus has at least two stage portions. Drive mechanism 21 is configured to provide relative movement between each of the stage portions and axis of rotation 15 in a direction perpendicular to axis of rotation 15. The method to compare similar physical areas of an inspection area includes the step of mounting samples 116, 118 on the stage apparatus such that there is one sample per stage portion. For example sample 116 is mounted on one stage portion and sample 118 is mounted on another stage portion. Samples 116, 118 are disposed symmetrically around axis of rotation 15. In the example presented here key points 120, 122 are directed in opposite directions and axis of rotation 15 is aligned midway between key points 120, 122. It should be noted that this method is applicable to inspection areas having more than two samples. It should also be noted that the repetitive physical areas of inspection area 115 are described as "similar physical areas" due to the fact that they are only identical to the extent that there are no defects on inspection area 115. The method also includes the step of scanning at least part of samples 116, 118 by employing scanning head 14 to perform a substantially circular scanning path 124. A radius 125 of circular scanning path 124 is typically at least the same as a radius 127 of samples 116, 118. The method also includes the step of comparing at least two best matched curved scan paths on circular scanning path 124, for example a curved scan path 126 and a curved scan path 128 by a pixel to pixel comparison. Circular scanning path 124 includes similar physical areas of both samples 116, 118. Therefore, a single swath produced by circular scanner 6 is useful for direct comparison between samples 116, 118 thereby making redundant the need to store large amounts of information. The method also includes the step of moving samples 116, 118 relative to axis of rotation 15 such that samples 116, 118 maintain a symmetrical disposition around axis of rotation 15 in order to perform an area scan of samples 116, 118. In the example presented here sample 116 is moved in a direction 130 and sample 118 is moved in a direction 132. If radius 125 is smaller than half of a distance 134 between the outer extremities of samples 116, 118, a synchronized rotation of samples 116 and 118 in a direction 136 and a direction 138 respectively is required in addition to the linear motion in directions 130, 132. It should be noted that the method referred to with reference to FIG. 9 is also applicable to a scanner having more than one scanning head and/or each scanning swath including more than one curved scanning path. It should also be noted that although the method illustrated with reference to FIG. 9 includes two samples 116, 118 the method is also applicable to using more than two samples.

Figure 10:
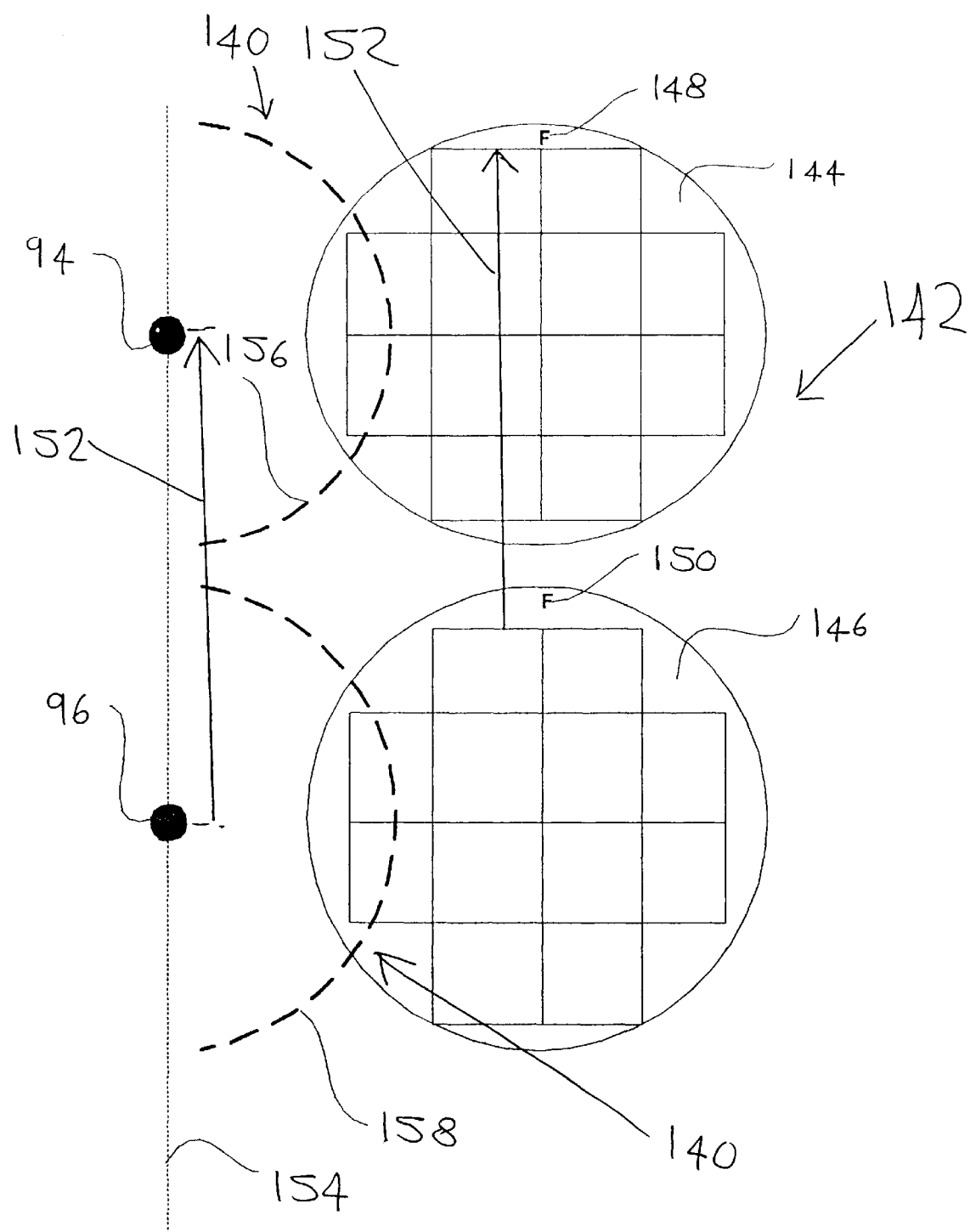
FIG. 10 is a schematic plan view of a scanning pattern of two samples produced by the operation of two circular scanners in accordance with a preferred embodiment of the invention.

Reference is now made to FIG. 10, which is a schematic plan view of a scanning pattern 140 of an inspection area 142 produced by scanning arrangement 5 in accordance with a preferred embodiment of the invention. Scanning arrangement 5 has two scanners, one of the two scanners including scanning head 90 and another of the two scanners including scanning head 92. Inspection area 142 includes a plurality of samples 144, 146. Samples 144, 146 are substantially identical to the extent that there are no defects on samples 144, 146. Samples 144, 146 have a substantially identical pattern. Sample 144 has a key point 148. Sample 146 has a key point 150. Key point 148 and key point 150 represent the same relative point on sample 144 and sample 146 respectively. In other words, key point 148 and key point 150 represent points of common symmetry of samples 144, 146. Samples 144, 146 are mounted on stage 19 such that key points 148, 150 are directed in the same direction. A repeat vector 152 represents the direction and distance of repetition of similar physical areas between sample 144 and sample 146. In other words, repeat vector 152 is the separation between key point 148 and key point 150. Axis of rotation 94 and axis of rotation 96 are separated by repeat vector 152. Axis of rotation 94 and axis of rotation 96 are connected by a line 154, which is parallel to repeat vector 154. Circular scanning of scanning head 90 produces a curved scanning path 156. Circular scanning of scanning head 92 produces a curved scanning path 158. Typically, curved scanning path 156 and curved scanning path 158 are produced simultaneously. Relative movement between stage 19 and axes of rotation 94, 96 is then generated in a direction which is perpendicular to repeat vector 88 and then another pair of curved scanning paths is produced. Therefore scanning pattern 140 is produced by simultaneous "double scan", where in each revolution of scanning heads 90, 92, two scanning swaths are produced that are separated from each other by repeat vector 152. The resulting curved scanning paths, for example curved scanning path 156 and curved scanning path 158, relate to similar physical areas of sample 144 and sample 146 and therefore curved scanning paths 156 and 158 are useful for direct comparison without the need to store large amounts of information. It is preferably for scanning head 90 and scanning head 92 to rotate in the same direction, thereby covering similar physical areas of inspection area 142. It is also preferable for the radius of curved scanning paths 156, 158 to b e large enough such that samples 144, 146 can be completely scanned without the need to rotate samples 144, 146. It should be noted that the method referred to with reference to FIG. 10 is also applicable a scanning arrangement having more than two circular scanners and therefore this method is used to scan more than two samples. It should be noted that the method referred to with reference to FIG. 10 is also applicable to each circular scanner having more than one scanning head and/or each scanning swath including more than one curved scanning path.

Figure 11:
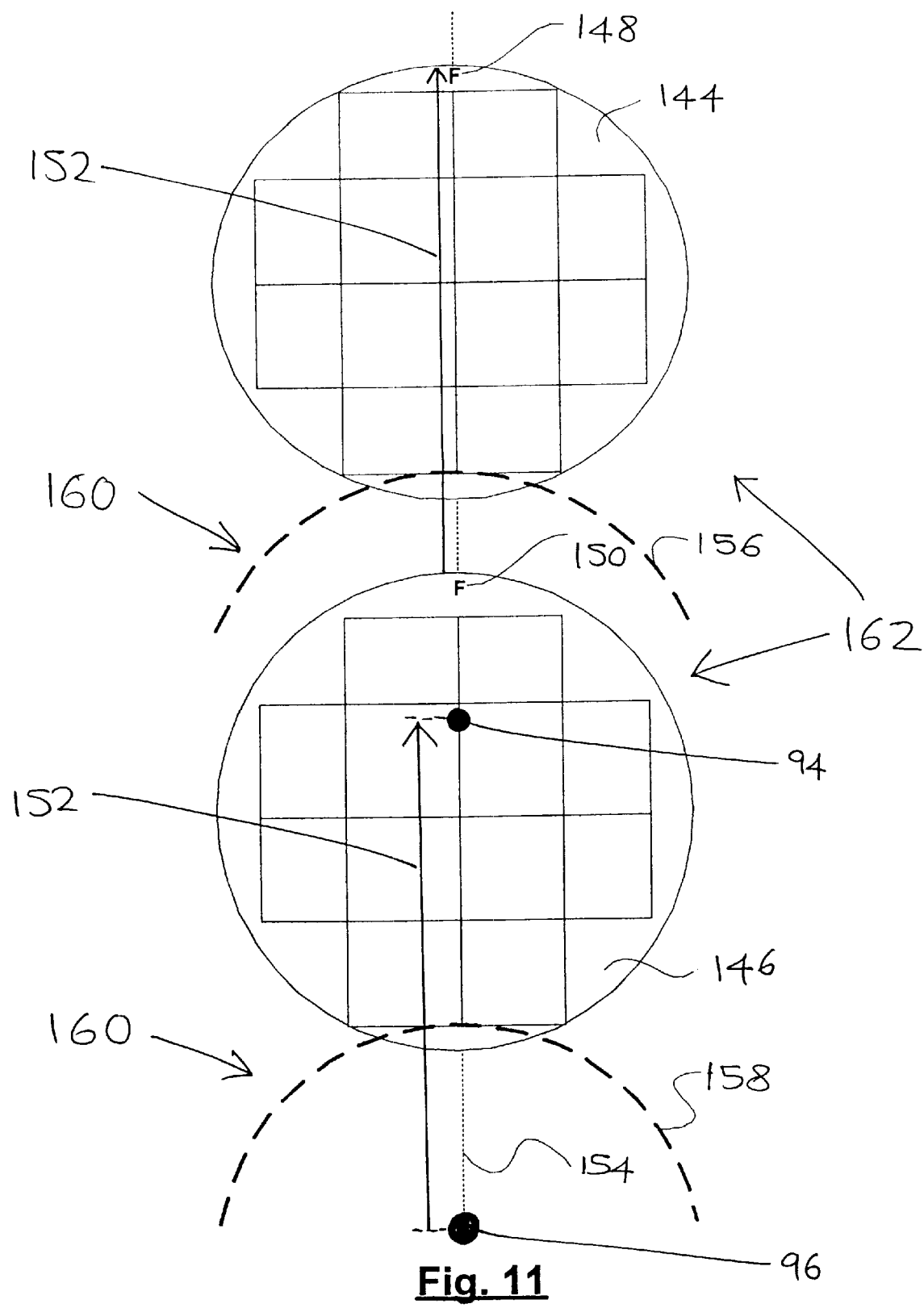
FIG. 11 is a schematic plan view of a scanning pattern of two samples produced by the operation of two circular scanners in accordance with an alternate embodiment of the invention.

Reference is now made to FIG. 11, which is a schematic plan view of a scanning pattern 160 of an inspection area 162 produced by scanning arrangement 5 in accordance with a preferred embodiment of the invention. Scanning arrangement 5 has two scanners, one of the two scanners including scanning head 90 and another of the two scanners including scanning head 92. Inspection area 162 includes samples 144, 146. The method to produce scanning pattern 160 is the same as the method used to produce scanning pattern 140 of inspection area 142 except that the relative movement between stage 19 and axes of rotation 94, 96 is generated in a direction which is parallel repeat vector 88.

Figure 12A:
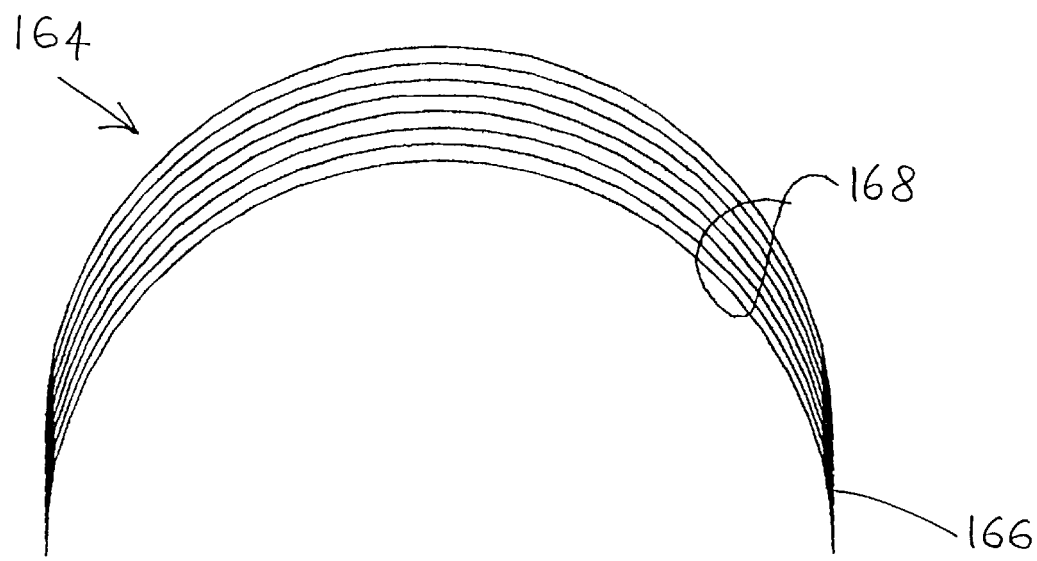
FIG. 12a is a schematic plan view of a scanning pattern produced by a circular scanning motion of a circular scanner whilst there is no relative linear motion between the stage and the axis of rotation of the circular scanner in accordance with the prior art.

Reference is now made to FIG. 12a, which is a schematic plan view of a scanning pattern 164 produced by a circular scanning motion of circular scanner 6 in accordance with the prior art. There is no relative linear motion between stage 19 and axis of rotation 15 of scanning head 14 while scanning pattern 164 is being produced. Scanning pattern 164 is produced by one scanning period of circular scanner 6 and scanning pattern 164 includes one scanning swath 166. Scanning swath 166 includes eight curved scanning paths 168. To produce an area scan, a relative linear "step" movement must be introduced between stage 19 and axis of rotation 15 of scanning head 14 between the production of scanning swaths by circular scanner 6. This process of "step" movement limits the processing speed of circular scanner 6 and therefore it is desirable to have constant relative linear movement between stage 19 and axis of rotation 15 of scanning head 14 during the whole scanning process even while circular scanner 6 is producing scanning swaths.

Figure 12B:
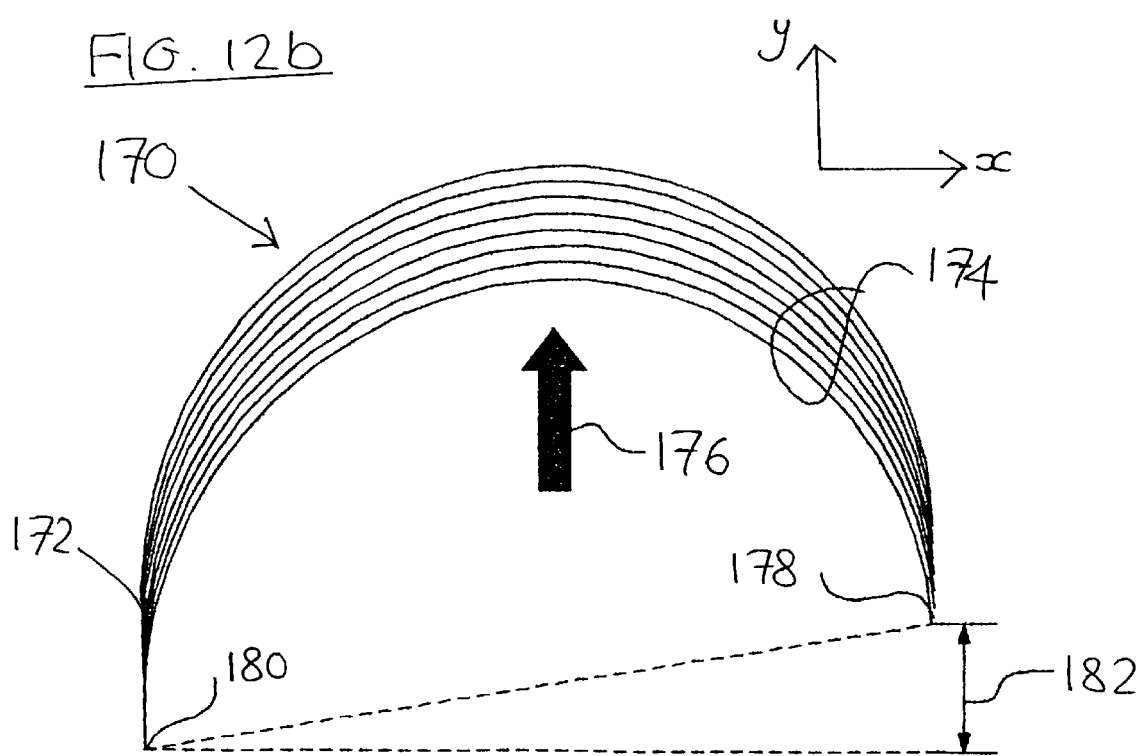
FIG. 12b is a schematic plan view of a scanning pattern produced by a circular scanning motion of a circular scanner combined with continuous relative linear motion between the stage and the axis of rotation of the circular scanner in accordance with a preferred embodiment of the invention.

Reference is now made to FIG. 12b, which is a schematic plan view of a scanning pattern 170 produced by a circular scanning motion of circular scanner 6 combined with continuous relative linear motion between stage 19 and axis of rotation 15 of scanning head 14 in accordance with a preferred embodiment of the invention. Scanning pattern 170 is produced by one scanning period of circular scanner 6. Scanning pattern 170 includes one scanning swath 172. Scanning swath 172 includes eight curved scanning paths 174. Scanning swath 172 is produced by a combination of circular motion of scanning head 14 about axis of rotation 15 and relative linear motion between stage 19 and axis of rotation 15 in a scan direction 176. Scan direction 176 is parallel to a y-axis. The y-axis is orthogonal to an x-axis. The linear motion along scan direction 176 is represented by a velocity vector $v_y(t)$. The velocity vector $v_y(t)$ changes the perfect circular shape of curved scanning paths 168 as shown with reference to FIG. 12a to a slightly different shape of curved scanning paths 174 as shown with reference to FIG. 12b. It is seen that an end point 178 of scanning swath 172 is shifted along scan direction 176 relative to a start point 180 of scanning swath 172 by a distance 182. Distance 182 is equal to $$\int_0^T v_y(t)\,dt$$

where and T is the time of one scanning period being the time taken to produce scanning swath 172 from start point 180 to end point 178.

Figure 13:
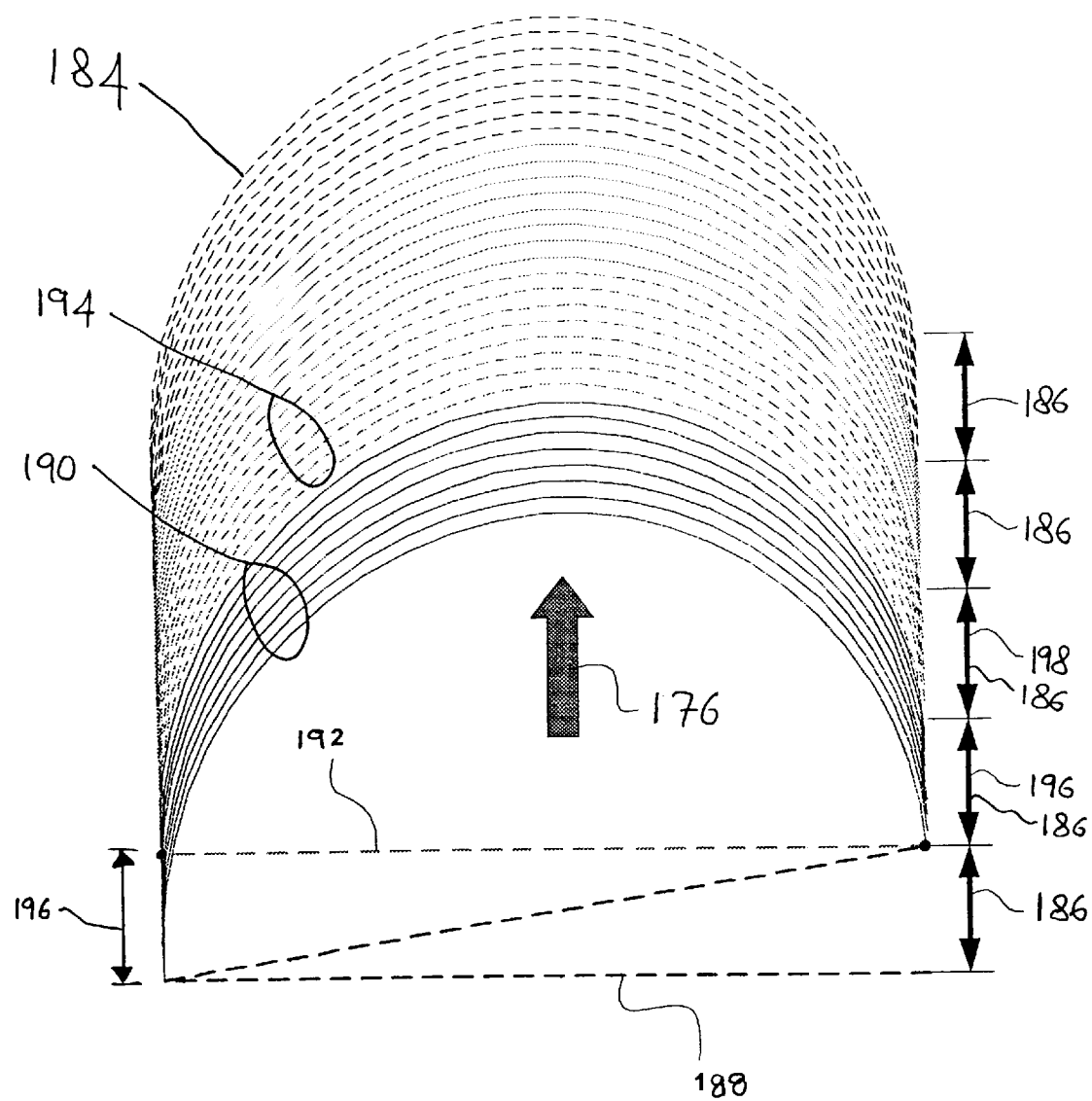
FIG. 13 is a schematic plan view of an area scanning pattern produced by the method of FIG. 12b.

Reference is now made to FIG. 13, which is a schematic plan view of an area scanning pattern 184 produced by the method of FIG. 12b. Area scanning pattern 184 is very useful for imaging purposes as area scanning pattern 184 gives substantially continuous coverage of an inspection area. Area scanning pattern 184 is produced by adjusting velocity vector $v_y(t)$ along scan direction 176 such that during time T a movement along scan direction 176 is equal to a distance 186. If velocity vector $v_y(t)$ is constant during time T, the magnitude of distance 186 is equal to velocity vector $v_y$ multiplied by time T. Continuous area scanning is produced by adjusting distance 186 such that distance 186 is substantially equal to the width of each of the scanning swaths. A line 188 indicates the position where a swath 190 starts. A line 192 indicates the position where swath 190 ends and a next swath 194 starts. A width 196 of swath 190 is equal to distance 186. A width 198 of swath 194 is equal to distance 186. In general, when distance 186 is equal to the width of each scanning swath, a position along scan direction 176 where one swath ends is the same position where the following swath starts. In this way a continuous area scan is produced by joining the scanning swaths one after the other. The scanning swaths are all perfectly aligned and create a continuous area scan without overlapping or gaps between the scanning swaths. It is clear that an image acquired by this method is different from a conventional image acquired by scanning along Cartesian coordinates. Therefore, look-up-tables are needed to convert the image data into a more conventional format. Moreover, area-scanning pattern 184 does not necessarily cover symmetrical physical areas of an inspection area. Therefore, the method used to produce area scanning pattern 184 is not useful for direct comparison between neighboring swaths without the need to store large amounts of information which is a major disadvantage of this method.

Figure 14:
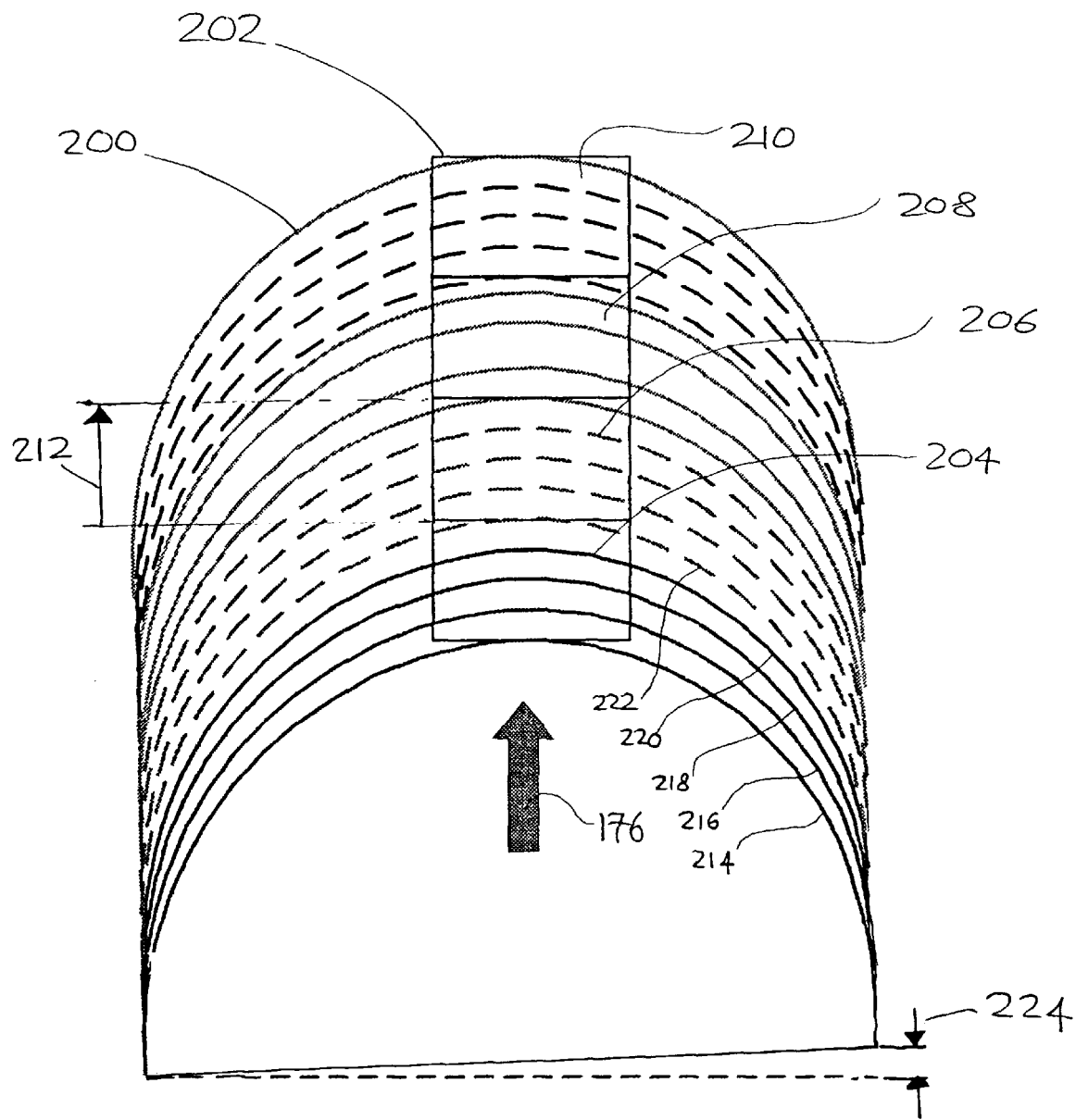
FIG. 14 is a schematic plan view of a low memory usage scanning pattern produced by a circular scanning motion of a circular scanner combined with continuous relative linear motion between the stage and the axis of rotation of the circular scanner in accordance with a preferred embodiment of the invention.

Reference is now made to FIG. 14, which is a schematic plan view of a low memory usage scanning pattern 200 of an inspection area 202 produced by a circular scanning motion of circular scanner 6 combined with continuous relative linear motion between stage 19 and axis of rotation 15 of scanning head 14 in accordance with a preferred embodiment of the invention. Inspection area 202 has a periodic pattern. The periodic pattern of inspection area 202 is represented by a plurality of rectangles 204, 206, 208, 210. The periodic pattern has a repeat vector 212. Repeat vector 212 represents the direction and distance of repetition of similar physical areas of inspection area 202. Therefore repeat vector 212 represents the direction and distance of repetition of rectangles 204, 206, 208, 210. It should also be noted that the repetitive physical areas of inspection area 202 are described as "similar physical areas" due to the fact that they are only identical to the extent that there are no defects on inspection area 202. A distance 224 is equal to the relative movement of stage 19 and axis of rotation 15 in the direction of repeat vector 212 during time T, the time taken to generate a scanning swath. Distance 224 is equal to velocity vector $v_y$ multiplied by time T.

In general, to enable comparison of similar physical areas of inspection area 202, scanning of inspection area 202 is performed by generating relative linear movement at constant velocity between stage 19 and axis of rotation 15 while at the same time performing circular scanning of scanning head 14 so as to generate scanning pattern 200 such that scanning pattern 200 includes a plurality of curved scanning paths wherein pairs of the curved scanning paths are related by an integer multiplied by repeat vector 212. To simplify the comparison process, scanning pattern 200 typically includes a plurality of scanning swaths wherein pairs of the scanning swaths are related by an integer multiplied by repeat vector 212. In other words, velocity vector $v_y$, being the relative velocity of stage 19 and axis of rotation 15 in the direction of repeat vector 212, is adjusted such that velocity vector $v_y$ is constant and a fourth integer multiplied by the time T, the time taken to generate a curved scanning path or scanning swath, is substantially equal to a fifth integer multiplied by a time taken to advance stage 19 relative to axis of rotation 15 by a distance equal to the length of repeat vector 212. In the illustration shown here, scanning pattern 200 includes a plurality of scanning swaths 214, 216, 218, 220, 222 each having a width W. Each of scanning swaths 214, 216, 218, 220, 222 includes at least one curved scanning path. It is seen that the fifth integer is equal to one and the fourth integer is equal to four. In other words, a movement in scan direction 176 equal to the size of repeat vector 212 is achieved during the execution of four scanning swaths 214, 216, 218, 220. Therefore, every fourth swath is compared as they relate to similar physical areas of inspection area 202. For example, scanning swath 214 and scanning swath 222 relate to similar physical areas and are therefore compared. The amount of memory required for the comparison is adjustable. The total amount of data to be stored in memory is a dependent on the total area covered by the swaths that are scanned within a distance of repeat vector 212. Typically, the available memory is not sufficient for storing all information contained within two or three consecutive sections of an inspection area. Therefore, it is clear that the inspection area should be scanned with a significant gap between the swaths by adjusting velocity vector $v_y$ or in other words distance 224 is typically much larger then width W.

Figure 15:
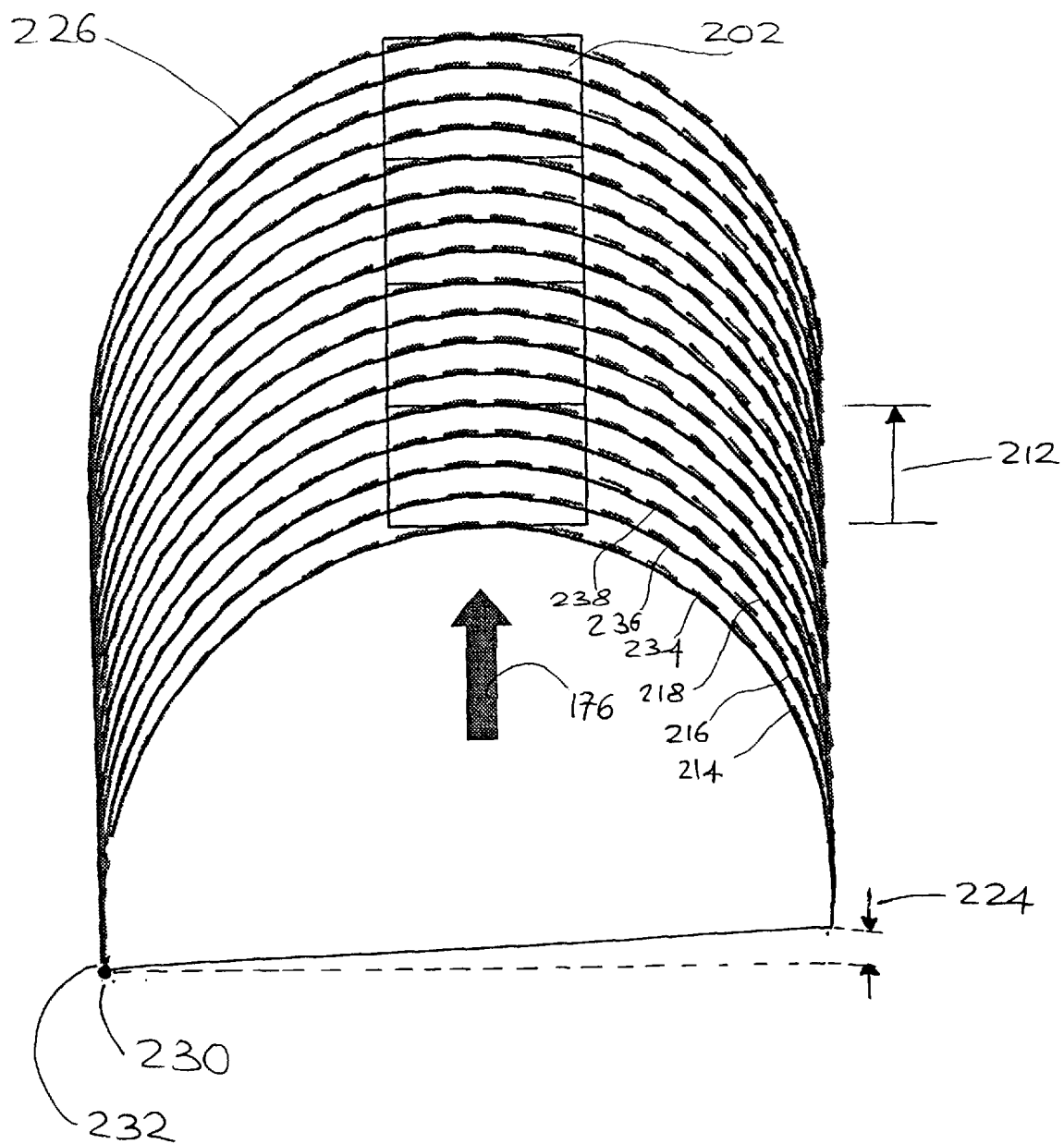
FIG. 15 is a schematic plan view of an area scanning pattern produced by the method of FIG. 14.

Reference is now made to FIG. 15, which is a schematic plan view of an area scanning pattern 226 of inspection area 202 produced by the method of FIG. 14. As mentioned with reference to FIG. 14, inspection area 202 is scanned with large gaps between scanned areas due to the condition that distance 224 is typically much larger then the width W of each swath. Therefore, in order to produce an area-scanning pattern that covers the whole of inspection area 202 several repetitions of the original scanning sequence are needed. Scanning pattern 200 (FIG. 14) is produced by the original scanning sequence starting at a position 230 (FIG. 15). Therefore, the first repetition of the scanning sequence starts at a position 232. Position 232 is separated from position 230 by a distance equal to width W parallel to scan direction 176. A very fast movement of stage 19 relative to axis of rotation 15, that is much higher than the normal relative movement of stage 19 and axis of rotation 15 during scanning, moves scanning head 14 to position 232 after the completion of the original scanning sequence. Area scanning pattern 226 includes a plurality of scanning swaths 234, 236, 238 produced by the first repetition of the scanning sequence. Due to the spacing between the original scanning sequence and the first repetition of the scanning sequence, scanning swath 234 is located immediately after scanning swath 214, scanning swath 236 is located immediately after scanning swath 216 and scanning swath 238 is located immediately after scanning swath 218. Scanning swaths 214, 216, 218 are represented as solid lines and the scanning swaths 234, 236, 238 are represented as dashed lines. Additional scanning sequences are performed until the whole of inspection area 202 is scanned. It should be noted that the method referred to with reference to FIGS. 14, 15 is also applicable to a scanner having more than one scanning head.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A method to compare similar physical areas of an inspection area of a sample using a scanning arrangement, the inspection area having a periodic pattern having a repeat vector, the scanning arrangement having a stage configured for mounting the sample thereon, the scanning arrangement having a drive mechanism and at least one circular scanner, the circular scanner having at least one scanning head and an axis of rotation, the scanning head performing a circular scanning motion about the axis of rotation, the drive mechanism configured to provide relative movement between the stage and the axis of rotation, the method comprising the steps of:
   (a) scanning the inspection area by a combination of circular scanning of the scanning head and by generating relative movement between the stage and the axis of rotation so as to generate a scanning pattern which includes a plurality of curved scanning paths wherein pairs of the curved scanning paths are related by an integer multiple of the repeat vector; and
   (b) comparing at least one of said pairs of the curved scanning paths by a pixel to pixel comparison.

2. The method of claim 1 wherein:
   (a) the at least one circular scanner is implemented as at least two circular scanners; and
   (b) the axes of rotation of said at least two circular scanners are separated by a multiple of the repeat vector.

3. The method of claim 2 wherein:
   (a) the axes of rotation of said at least two circular scanners are connected by a line which is parallel to the repeat vector; and
   (b) said relative movement between the stage and the axes of rotation is generated in a direction which is parallel to the repeat vector.

4. The method of claim 2 wherein:
   (a) the axes of rotation of each of said at least two circular scanners are connected by a line which is parallel to the repeat vector; and
   (b) said relative movement between the stage and the axis of rotation is generated in a direction which is perpendicular to the repeat vector.

5. The method of claim 4 wherein the axes of rotation of said at least two circular scanners are separated by a distance substantially equal to a diameter of each of the curved scanning paths.

6. The method of claim 4 wherein the axes of rotation of said at least two circular scanners are separated by a distance less than a diameter of each of the curved scanning paths.

7. The method of claim 2 wherein:
   (a) the inspection area includes a plurality samples which are substantially identical, each of said samples having a key point, the repeat vector being the separation between key points of said samples; and
   (b) the method further includes the step of mounting said samples on the stage such that the key points of said samples are directed in the same direction.

8. The method of claim 1 wherein the step of scanning the inspection area is performed by scanning the inspection area by generating relative linear movement between the stage and the axis of rotation while at the same time performing circular scanning of the scanning head so as to generate a scanning pattern which includes a plurality of curved scanning paths wherein pairs of the curved scanning paths are related by an integer multiple of the repeat vector.

9. The method of claim 8 wherein said relative linear movement is at constant velocity.

10. The method of claim 8 wherein a first integer multiplied by a time taken to generate one of the curved scanning paths is substantially equal to a second integer multiplied by a time taken to advance the stage relative to the axis of rotation by a distance equal to the length of the repeat vector.

11. The method of claim 10 wherein said second integer is equal to one.

12. A method to compare similar physical areas of an inspection area using a circular scanner, the inspection area including a plurality of samples, the samples being substantially identical, the circular scanner having a stage apparatus, a drive mechanism, at least one scanning head and an axis of rotation, the at least one scanning head performing a circular scanning motion about the axis of rotation, the stage apparatus having at least two stage portions, the drive mechanism configured to provide relative movement between each of the stage portions and the axis of rotation, the method comprising the steps of:
   (a) mounting the samples on the stage apparatus such that there is one of the samples per one of the stage portions such that said samples are disposed symmetrically around the axis of rotation;
   (b) scanning at least part of the samples by employing the scanning head to perform a substantially circular scanning path;
   (c) comparing at least two best matched curved scan paths on said substantially circular scanning path by a pixel to pixel comparison; and
   (d) moving the samples relative to the axis of rotation such that said samples maintain a symmetrical disposition around the axis of rotation.

* * * * *